(12) United States Patent
Xu et al.

(10) Patent No.: US 7,340,119 B1
(45) Date of Patent: Mar. 4, 2008

(54) OPTICAL SENSOR AND SYSTEM

(75) Inventors: Chang-Qing Xu, Dundas (CA); Jian Yang, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 106 days.

(21) Appl. No.: 11/407,252

(22) Filed: Apr. 20, 2006

Related U.S. Application Data

(60) Provisional application No. 60/672,847, filed on Apr. 20, 2005.

(51) Int. Cl.
*G02B 6/00* (2006.01)

(52) U.S. Cl. .............................. 385/12; 385/13; 385/37
(58) Field of Classification Search ............ 385/12–13, 385/37; 250/227.14
See application file for complete search history.

(56) References Cited

U.S. PATENT DOCUMENTS 6,965,708 B2 * 11/2005 Luo et al. ..................... 385/12
7,068,868 B1 * 6/2006 Pi et al. ........................ 385/12
2005/0002606 A1 * 1/2005 James et al. .................. 385/31
2007/0025661 A1 * 2/2007 Wang et al. ................... 385/37

OTHER PUBLICATIONS

Ignacio Del Villar, et al.; Optimization of Sensitivity in Long Period Fiber Gratings With Overlay Deposition: Optics Express, vol. 13, No. 1, Jan. 10, 2005, pp. 56-69.

* cited by examiner

*Primary Examiner*—Hemang Sanghavi

(57) ABSTRACT

An optical sensor has a core, a cladding, and an over-layer. In some embodiments the optical sensor also has a sensing layer. The over-layer acts as a sensitivity enhancement layer, with a refractive index larger than that of the cladding layers. A periodic structure, such as a long-period grating (LPG), is formed in the core. A transmission spectrum of the device shows several notches due to the existence of the LPG. A change in the sensing layer's refractive index and/or thickness results in a shift in the notch wavelengths of the LPG. By choosing proper refractive indices and thicknesses of the core, the cladding and the over-layer, the shift in the notch wavelengths can be significantly enhanced.

20 Claims, 5 Drawing Sheets

OPTICAL SENSOR AND SYSTEM

CROSS-REFERENCE TO RELATED APPLICATIONS

This application claims the benefit of U.S. Provisional Application No. 60/672,847 filed Apr. 20, 2005 which is hereby incorporated by reference.

FIELD OF THE INVENTION

The invention relates to optical sensors which have applications in the fields of medicine and biomedicine.

BACKGROUND OF THE INVENTION

Optical sensors are devices that can be used to detect the change in an ambient environment and/or existence of analytes in the ambient environment. For example, if the sensor is formed with a biologically derived binding agent that has selective chemical or biological interaction with a certain analyte, a biosensor can be formed. Biosensors have attracted considerable attention recently due to their potential applications in medical diagnostics, explosives detection, determination of food quality, genetic screening and environmental monitoring.

To date, many optical sensors have been proposed and demonstrated. Long-period grating (LPG) and fiber Bragg grating (FBG) based on the evanescent wave are two major techniques that are widely used in fiber optical sensors. In these sensors, a periodic structure is written in the fiber structure, and a change of the analyte changes the optical field in the fiber structure. This results in a change in reflection and/or transmission spectrum of the periodically modulated fiber. Fiber optical sensors have attracted much attention recently due to their excellent characteristics such as compatibility with the standard optical fiber and simple fabrication process.

Fiber optic long period gratings are photonic devices usually made by UV induced refractive index modulation in the core of optical fiber. Light is coupled between the fundamental guiding mode and the co-directional cladding mode of the fiber at specific wavelengths. Because of the high loss due to scattering in the cladding mode propagation, the light coupled out of the core mode is lost before it is able to couple back to the guiding mode and thus leaves an absorption notch at the corresponding wavelengths (i.e., the mode coupling wavelength) in the transmission spectrum. The sensing mechanism arises from the dependence of the mode coupling wavelength on the effective index of the guiding mode and the cladding mode, as well as the period of the periodic modulation to the refractive index of the fiber core. One unique feature of LPGs is their high sensitivity to the ambient refractive index surrounding the cladding of the optical fiber. It is for this reason that LPGs have been widely accepted for fiber optic refractive index measurements. An important development of this sensing structure is the ability to deposit a layer of biorecognition material which can change its refractive index upon analyte binding. This method has been applied for chemical sensing and for sensitive detection of antibody-antigen reactions.

Enhancing sensitivity is a key issue in the development of optical sensors and is especially important when the change in the ambient environment or in volume (e.g. size or concentration) of analyte is small. A surface plasmon resonance (SPR) is usually used to enhance sensitivity of optical sensors.

SPR is an optical phenomenon caused by charge density oscillations at the interface between two media with dielectric constants of opposite sign, such as a metal and a dielectric such as glass for example. When light of an appropriate wavelength interacts with the dielectric-metal interface at a defined angle, called the resonance angle, there is a match of resonance between the energy of the light photons and the electrons at the metal surface. This resonance is experimentally observed as a sharp minimum in light reflectance when the angle of incidence is varied. Alternatively, SPR can also be generated by use of a fixed angle white light source with a broad bandwidth, using spectral detection. Any change in the refractive index of absorbed layers at the metal surface will affect the SPR coupling conditions and produce a shift in the resonance conditions.

In SPR fiber optical sensors, the cladding of the fiber is partially removed and a gold layer is deposited symmetrically around the exposed fiber core. Despite the successful demonstration of high sensitivity SPR sensors based on bulk and planar waveguide devices, high performance fiber-optic SPR sensors have not been reported mainly due to difficulties in device fabrication and operation. It is difficult to deposit a homogeneous coating and achieve good chemical functionality when using a round surface such as that of a fiber. Stable signals are also difficult to achieve since the SPR resonance condition is strongly dependent on the polarization state of the light propagating in the fiber, the polarization state being difficult to control within fibers. Furthermore, due to the critical SPR conditions, the wavelength used for sensing is usually shorter than 1 μm. Generally, low-cost high-performance tunable and/or broadband light sources required for fiber optic SPR biosensors are not commercially available.

Since only a small portion of a light field propagates as the evanescent wave along the fiber, LPG sensors usually have low sensitivity as compared with the SPR sensors. As a result, LPG biosensors are usually used to detect large molecules that provide larger refractive index change experienced by the evanescent wave.

SUMMARY OF THE INVENTION

Some embodiments of the invention provide an optical sensor having a core, at least one cladding layer, at least one high refractive index over-layer and at least one sensing layer. The high refractive index over-layer acts as a sensitivity enhancement layer, with a refractive index larger than that of the cladding layers. A periodic structure such as a long-period grating (LPG) is formed in the core layer. The transmission spectrum of the device shows several notches due to the existence of the grating. A change in the sensing layer's refractive index and/or thickness results in a shift in the notch wavelengths. By choosing proper refractive indices and thicknesses of the core, the cladding and the high refractive index over-layer, the shift in the notch wavelengths can be significantly enhanced.

According to one broad aspect, the invention provides an optical sensor comprising: a core; a cladding, the cladding and the core collectively comprising an optical waveguide; an over-layer over the cladding having a refractive index greater than that of the cladding; a periodic structure in at least one of the core and the cladding; a sensing layer over the over-layer made of a sensing material that has an index of refraction that changes as a function of ambient environment.

In some embodiments, the over-layer is adapted to serve as a sensitivity enhancement layer.

In some embodiments, the optical sensor is formed on a planar substrate.

In some embodiments, the cladding comprises a first cladding layer and a second cladding layer, the first cladding layer being in close proximity to the planar substrate and the second cladding layer being in close proximity to the over-layer.

In some embodiments, the optical sensor is formed on an optical fiber.

In some embodiments, a notch wavelength shift as a function of over-layer thickness has at least one section with relatively poor sensitivity enhancement, at least one section with relatively good sensitivity enhancement, and at least one section that is systemically poor for sensing, and wherein the over-layer thickness is selected to be in the at least one section with relatively good sensitivity enhancement.

In some embodiments, the periodic structure is in the core.

In some embodiments, the periodic structure is in the cladding.

In some embodiments, the periodic structure is a long-period grating.

In some embodiments, the periodic structure is a fiber Bragg grating.

In some embodiments, the optical sensor further comprises a jacket.

In some embodiments, the radius of the fiber core is 4.1 μm and the outer radius of the cladding is 62.5 μm.

In some embodiments, the periodic structure has a step index profile with a relative index difference of 0.34%.

In some embodiments, the over-layer is deposited on the cladding, and the sensing layer is deposited on the over-layer.

In some embodiments, the over-layer has an index of refraction greater than the second cladding layer.

In some embodiments, the index of fraction and/or thickness of the over-layer are selected to optimize operating conditions such as sensitivity, refractive index of the sensing layer.

According to another broad aspect, the invention provides apparatus for determining a measurable parameter experienced by a remote light sensor comprising: a light source, an optical sensor for receiving light transmitted by the light source, the optical sensor comprising a core, a cladding, the cladding and the core collectively comprising an optical waveguide and an over-layer over the cladding having a refractive index greater than that of the cladding, a sensing layer over the over-layer made of a sensing material that has an index of refraction that changes as a function of ambient environment; the optical sensor further comprising a periodic structure in at least one of the core and the cladding; and a detector for receiving a light signal output by the optical sensor.

In some embodiments, the index of fraction and/or thickness of the over-layer are selected to optimize operating conditions.

According to another broad aspect, the invention provides a method comprising: immersing an optical sensor in an ambient environment, the sensor comprising a core, a cladding, the cladding and the core collectively comprising an optical waveguide, an over-layer having a refractive index greater than that of the cladding; a periodic structure in at least one of the core and the cladding, and a sensing layer made of a sensing material that has an index of refraction that changes as a function of ambient environment; inputting a broadband light source to the sensor; measuring a transmission spectrum characteristic and mapping the transmission spectrum characteristic to a characteristic of the ambient environment.

BRIEF DESCRIPTION OF THE DRAWINGS

Various embodiments of the invention will now be described with reference to the attached drawings in which.

DETAILED DESCRIPTION OF THE EMBODIMENTS

Figure 1A:
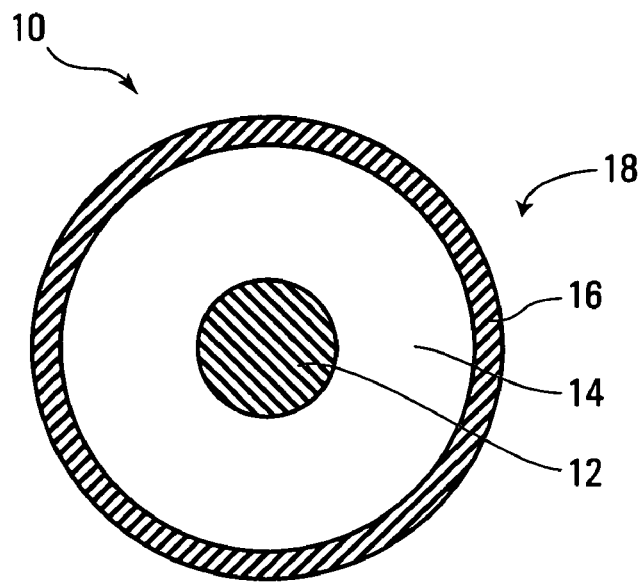
FIG. 1A is a transverse cross section of a three-layer structure of a conventional biosensor.
Figure 1B:
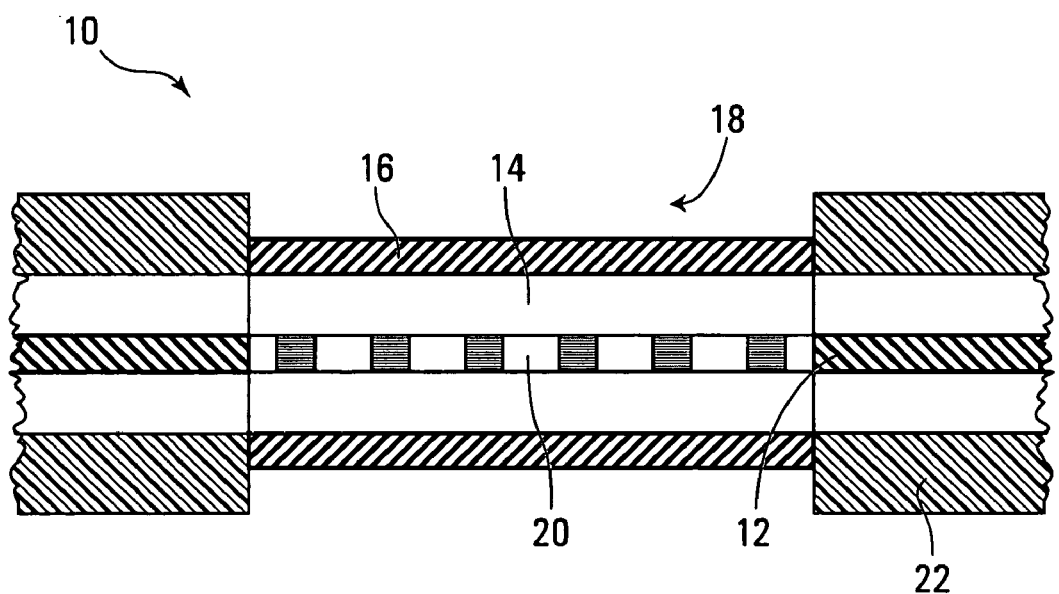
FIG. 1B is a longitudinal cross section of the three-layer structure of FIG. 1A.

Referring to FIGS. 1A and 1B, shown are transverse and longitudinal cross sections, respectively, of a conventional optical fiber biosensor 10. Biosensor 10 has a core 12, a cladding 14, and a sensing layer 16. Optical fiber biosensor 10 is essentially two concentric cylinders, the inner cylinder being core 12 and the outer cylinder cladding 14, with sensing layer 16 being deposited on the exterior of cladding 14. Core 12 has a long-period grating 20. Sensing layer 16 is exposed to an ambient environment 18. A jacket 22 surrounds biosensor 10 at both ends of the device.

Various optical sensors in accordance with embodiments of the invention will now be described.

Four-Layer Structure

Figure 2A:
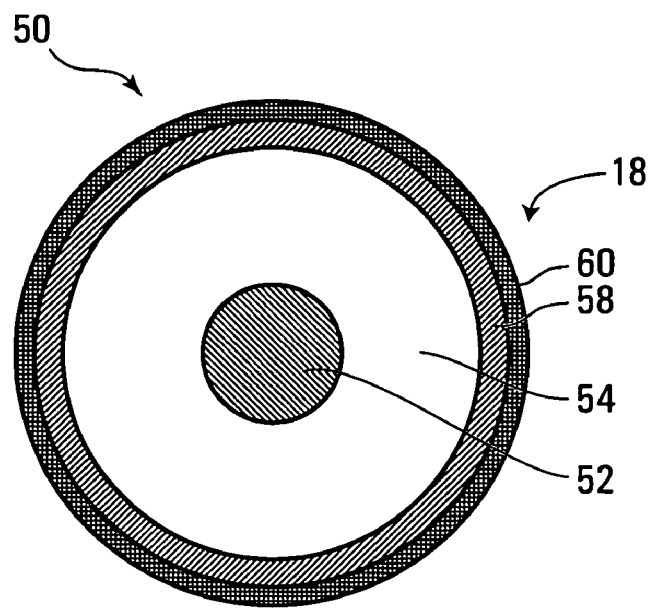
FIG. 2A is a transverse cross section of a four-layer structure of a sensitivity enhanced biosensor, according to an embodiment of the invention.
Figure 2B:
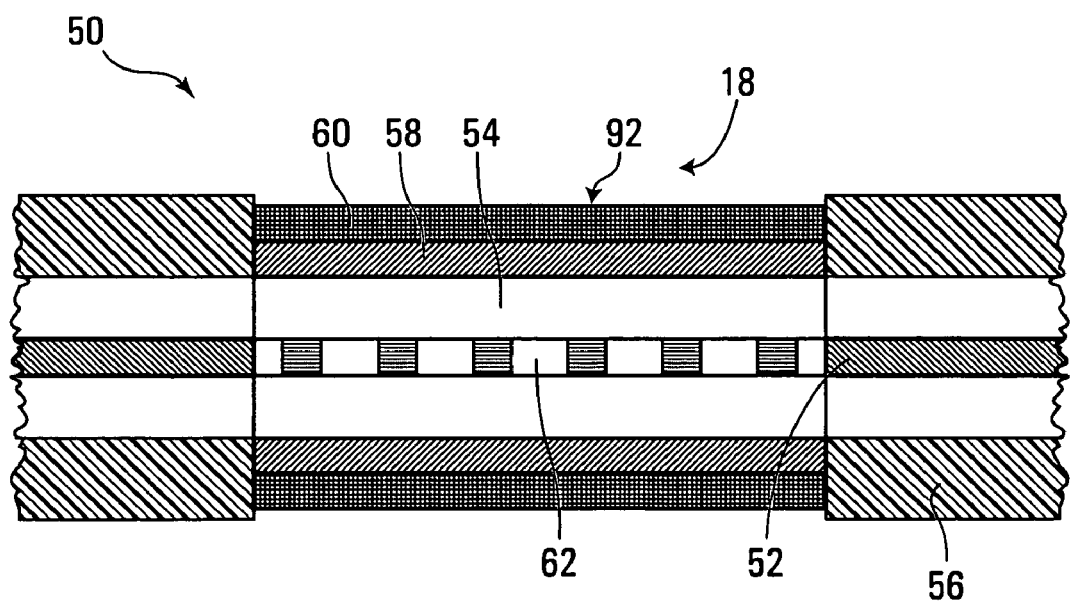
FIG. 2B is a longitudinal cross section of the four-layer structure of FIG. 2A.

Referring to FIGS. 2A and 2B, shown are transverse and longitudinal cross sections, respectively, of an optical sensor in the form of a four-layer structure of a sensitivity enhanced biosensor 50, according to an embodiment of the invention. The structure is formed on an optical fiber having a core 52, a cladding 54 (more generally at least one cladding layer) and a jacket 56. In a biosensing portion 92 of the optical fiber there is a high refractive index over-layer 58 (more generally, at least one high refractive index over-layer), and a sensing layer 60 (more generally at least one sensing layer) exposed to an ambient environment 18 for biochemical and/or chemical sensing. Core 52 has a periodic structure which in this case is a long-period grating 62. A fiber Bragg grating can also be used.

Advantageously, in some embodiments, the over-layer properties for the four-layer structure can be fine tuned for different sensing materials (in terms of refractive index and thickness of the sensing materials) by selecting a proper refractive index and thickness of the over layer.

Figure 4:
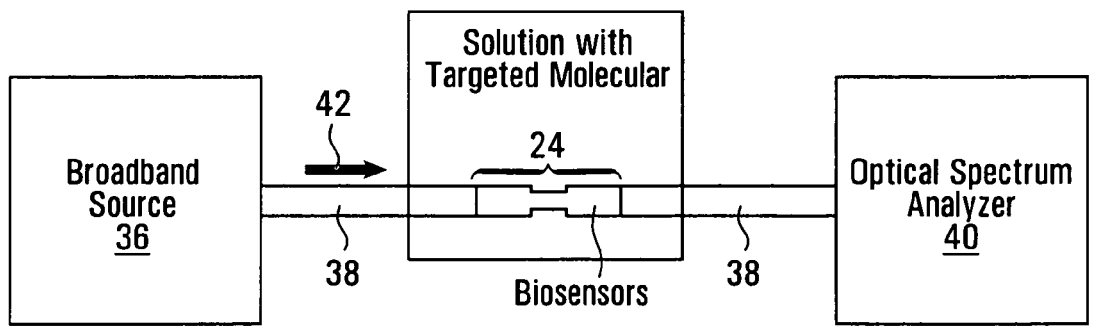
FIG. 4 is a block diagram of a system for use with the sensitivity enhanced refractometer of FIG. 2A.

In an example implementation the sensor 24 of FIGS. 2A and 2B is used in connection with a system shown in FIG. 4. The system of FIG. 4 has a broadband source 36, optical fibers 38, the sensor 50 of FIGS. 2A and 2B, and an optical spectrum analyser 40. Broadband source 36 provides output light 42 that propagates through optical fibers 38 and refractometer 24. Spectrum analyser 40 analyses the light received so as to detect changes in the ambient environment. In a particular example, output light 42 is of a wavelength centred around 1550 nm; however, it is to be clearly understood that other wavelengths can be used. It is also to be clearly understood that any suitable light source and any suitable detector can be used. Furthermore, embodiments of the invention are not limited to using sensor 24 of FIGS. 2A and 2B with broadband source 36 and optical spectrum analyser 40, and in other embodiments of the invention other optical sensors are used.

Parameters

In an example implementation of the sensor 50 of FIGS. 2A and 2B, the radius of fiber core 52 is 4.1 µm, and the outer radius of cladding layer 54 is 62.5 µm as for most conventional optical fibers. The refractive index and material dispersion of cladding layer 54 of the optical fiber is represented by a linear fit of a Sellmeier formula refractive index curve for fused silica. For this example, the refractive index of fiber core 52 is assumed to have a step index profile with a relative index difference of 0.34%. A high refractive index material, in this case with its refractive index around 1.70 is deposited on fiber cladding 54 as over-layer 58. Above over-layer 58 is a layer of sensing material with its thickness arbitrarily selected to be 50 nm, which would change its refractive index and/or thickness upon its interaction with specific chemicals. In this case, it is assumed that the refractive index of the material changes from 1.44 to 1.54 in a reaction.

The particular material used as a sensing material is implementation specific. Particular examples include an immobilized antibody for detection of antigen or pesticide; a ssDNA or aptamer for detection of CDNA or the target molecule.

Parameter Simulation

In some embodiments, parameters of the sensor can be optimized by simulation. For example, the thickness of the over-layer can be simulated with various values to determine a value that yields the best sensitivity. In a particular simulation instance, the thickness of the high refractive index material was scanned from 0 nm to 500 nm in a simulation to allow the selection of a particular thickness that yields the best sensitivity enhancement. In the simulation, ambient environment 18 was selected to be pure water, and its refractive index and material dispersion is given by the linear fitted Sellmeier formula for the refractive index of pure water.

For purposes of simulation, the photosensitivity of the fiber is assumed to have a step function profile in the fiber core, which is azimuthally uniform. The LPG has a length of 25.4 mm without any chirp or phase shift. The refractive index modulation of the LPG is a non-apodized uniform modulation with a period of 375 µm and its duty-cycle is 50%. The amplitude of the refractive index modulation is $5\times10^{-4}$ without any DC bias.

Figure 3:
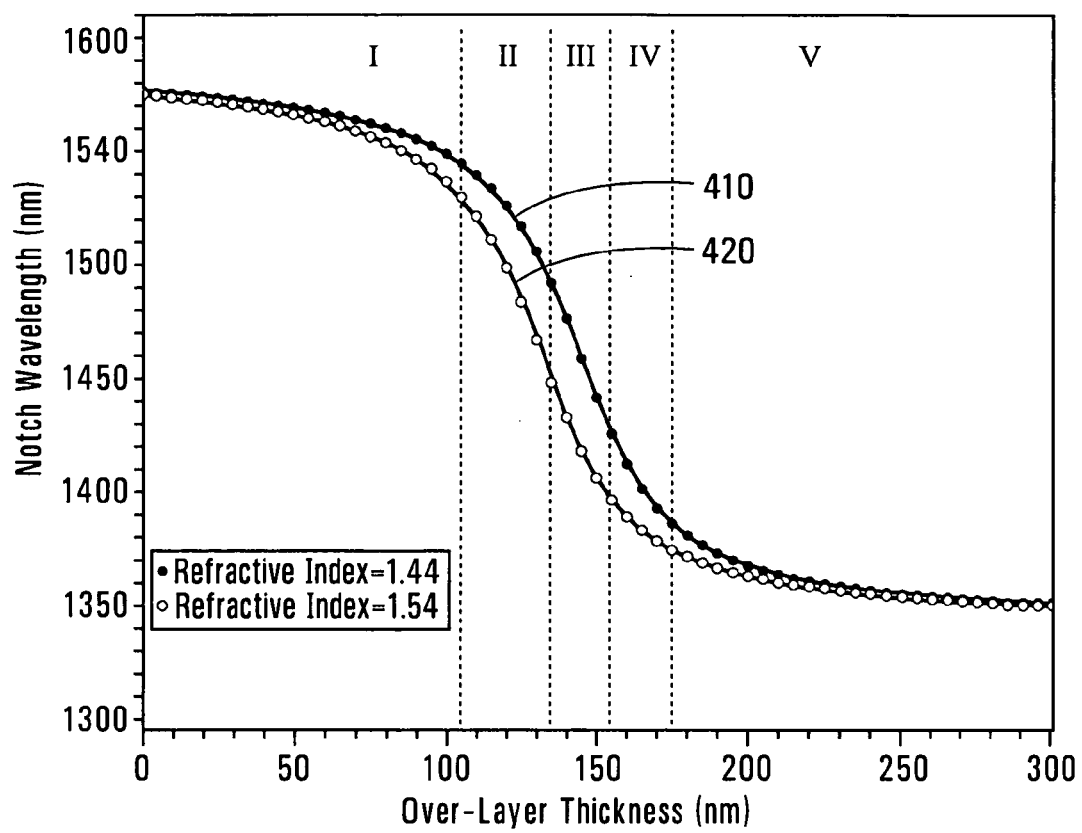
FIG. 3 is a graph of notch wavelengths obtained from simulation results and plotted as a function of over-layer thickness for the three-layer structure of FIG. 2A.

Referring to FIG. 3, shown is a graph of notch wavelengths obtained from simulation results and plotted as a function of over-layer thickness for the three-layer structure of FIGS. 2A and 2B. Results are shown for two different refractive indexes at opposite ends of the range for the sensing material (R.I.=1.44 for curve 410 and R.I.=154 for curve 420). The results show that insertion of a high refractive index layer not only shifts the resonance notch wavelength but also enhances the sensitivity of the notch wavelength shift upon a change of the refractive index of the sensing layer. For the illustrated example, the operation of the high refractive index over-layer enhanced LPG sensor can be divided into five working zones, as marked I-V in FIG. 3. In zone I, starting from 0 nm as the thickness of the high refractive index over-layer increases, the notch wavelength of the LPG shift towards shorter wavelengths, and its sensitivity upon the change of the sensing layer's refractive index increases moderately. In zone II, as the thickness of the over-layer reaches a certain value, in this case ~105 nm, the notch wavelength of the LPG sensor shifts rapidly towards shorter wavelengths and the sensitivity of the LPG is greatly enhanced by the change in the sensing layer's refractive index. In zone III, which is located in the over-layer thickness between 135 nm and 155 nm, the notch wavelength continues to rapidly shift towards shorter wavelengths. However, for the particular set of parameters being simulated, the depth of the notch for these thicknesses becomes very small, and as such this range is not appropriate for sensing. In zone IV, the notch structure of the LPG spectrum shows up for short wavelengths at the over-layer thickness of 155 nm and shifts toward shorter wavelengths with increasing over-layer thickness. The sensitivity of the LPG to the change in the sensing layer's refractive index is very high, and it decreases with increasing over-layer thickness. In Zone V, where the thickness of the sensing enhancement layer is between 185 nm and 500 nm (plot only shows to about 300 nm) at the upper limit of the study, the notch wavelength of the LPG transmission spectrum shifts towards a saturation wavelength of approximately 1350 nm. At this stage, wavelength shift sensitivity as a function of the change of the sensing layer refractive index change becomes minor and is not useful for sensing.

Suggested Operating Region

In FIG. 3, the sensitivity of the over-layer enhanced chemical/biochemical LPG sensor to the change in the sensing layer's refractive index is associated with the slope of the notch wavelength vs. over-layer thickness curve. Higher wavelength vs. over-layer thickness curve slope brings in higher sensitivity of the notch wavelength shift to a change in the sensing layer's refractive index. Based on this, it is preferable to select zone II and zone IV in FIG. 3 for the application of chemical/biochemical LPG sensing based on the change of the sensing layer's refractive index.

More generally, for an arbitrary implementation, zones similar to those of FIG. 3 can be defined as a function of over-layer thickness. Curves that plot wavelength shift as a function of over-layer thickness may include one or more sections with relatively poor sensitivity enhancement, for example due to low slope (regions I and V of the above example), one or more sections with relatively good sensitivity enhancement, for example due to larger slope (regions II and IV) of the above example. There may also be one or more sections that are systemically poor for sensing, such as where the notch depth becomes poor for sensing. It is not theoretically well understood why there is a range of over-layer thickness that results in poor sensing performance due to reduced notch depth. In one theory, the core modes and cladding modes are assumed to experience destructive interference for these conditions; in another theory, it is assumed that more power propagates in cladding modes resulting in less reflection/absorption by the periodic structure. These sections are not precisely defined. What constitutes "relatively good" and "relatively poor" can be defined on an implementation specific basis. In some implementations, the over-layer thickness is selected to be in one of the sections with relatively good sensitivity enhancement.

It is to be clearly understood that different dimensions and materials can be used for cladding 54, core 52, over-layer 58, and sensing layer 60 of the structures of FIGS. 2A, and 2B, and that the above dimensions, materials and material properties are given as examples only.

The structures of FIGS. 2A, and 2B are formed on optical fibers. In other embodiments of the invention, optical sensors such as the biosensors of FIGS. 2A and 2B are formed as planar structures, as shown for example in FIG. 2C.

Figure 2C:
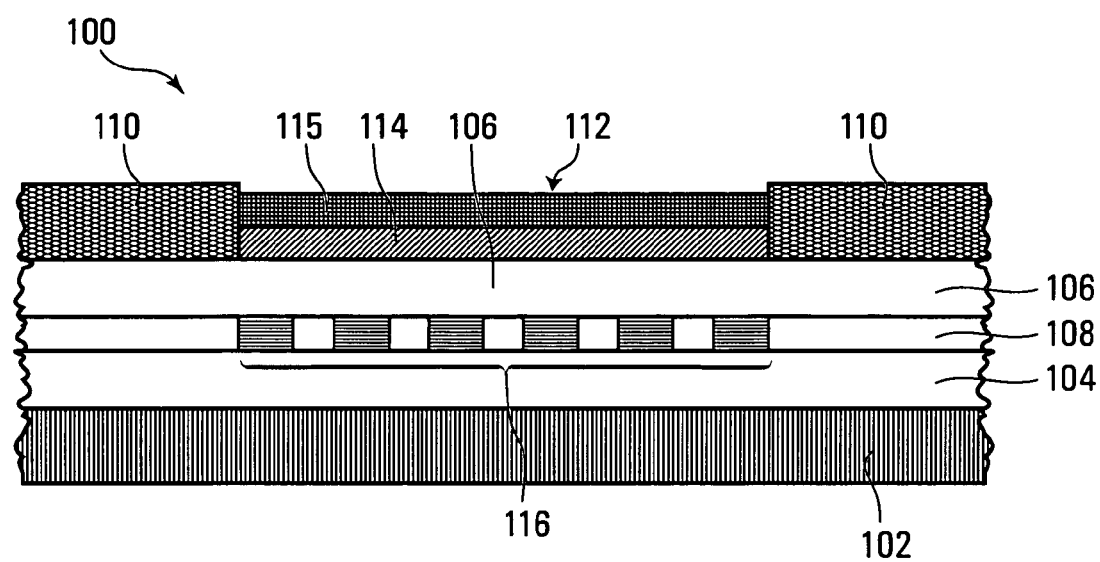
FIG. 2C is a longitudinal cross section of a planar structure of a sensitivity enhanced biosensor, in accordance with another embodiment of the invention.

Referring to FIG. 2C, shown is a planar structure of a sensitivity enhancing biosensor 100, in accordance with yet another embodiment of the invention. The planar structure is formed on a planar substrate 102 and has a first cladding layer 104, a core layer 108, a second cladding layer 106, and a jacket 110. A sensing portion 112 of the planar structure has an over-layer 114 having an index of refraction that is greater than that of the second cladding layer 106. The sensing portion 112 also has a sensing layer 115. In the sensing portion 112, the core layer 108 has a periodic structure, such as a long-period grating 116.

Figure 5:
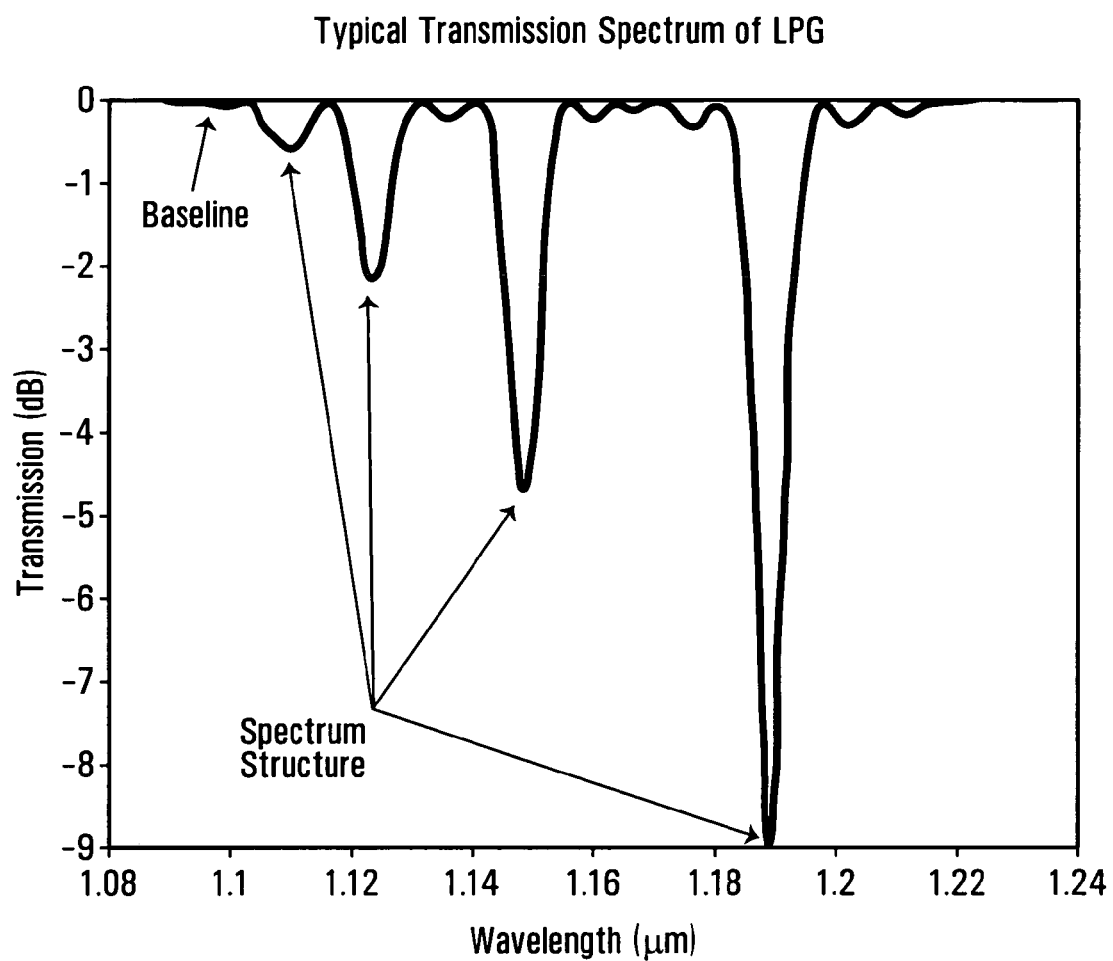
FIG. 5 is a plot of an example of an LPG transmission spectrum.

Referring now to FIG. 5, shown is a plot of an example transmission spectrum of an LPG that might be used in the core of one of the sensors described above. Of course, the actual spectrum will be implementation specific. In the illustrated example, the spectrum includes four notches. The notch to the right (at approximately 1.19 µm) is the sharpest and deepest and as such this would be the best notch for sensing purposes, but other notches, or combinations of notches may be employed. When the sensor is immersed in the ambient environment being tested, the wavelength of the notch will shift. In order to translate this into a useful reading, calibration can be performed that associates specific shifts in the notch wavelength with particular concentrations of the molecule being tested.

The broadband source needs to have a bandwidth that spans the location of the notch of interest, and locations to which it might shift. Thus, it is not necessary that the broadband source cover the entire spectrum, such as that of FIG. 5; rather the bandwidth might be centred at or near the notch wavelength of interest. Examples of broadband sources include commercially available superluminous LEDs at 0.8, 1.31 and 1.5 µm. These LEDs have a bandwidth of approximately 50 nm. Another broadband source that can be used is the ASE (amplified spontaneous emission) generated by an EDFA (Erbium doped fiber amplifier) with no input.

In some embodiments, the structure of the sensor is tailored to a particular broadband source. For example, if it is known that a 1.5 µm broadband source is to be employed, the LPG, over-layer and or sensing layer can all be selected such that the notch wavelength falls within the bandwidth of the selected broadband source.

There are many applications of biosensors. For example, if a sensing layer formed in the above described four-layer structure is selectively reacted with a target molecular, the refractive index and/or thickness of the sensing layer will be changed. As a result, transmission spectrum of the LPG will be changed. The proposed sensor can be used to detect the existence of a targeted molecular. This type of sensor for example may find applications in medical diagnosis.

In FIGS. 2A, 2B and 2C, the long-period grating is located in the core. However, it is to be clearly understood that the grating need not be in the core. For example, in other embodiments of the invention the grating is in the cladding. In yet other embodiments of the invention the grating is in both the core and the cladding. Furthermore, other periodic structures, such as fiber Bragg gratings for example, can be used.

Numerous modifications and variations of the present invention are possible in light of the above teachings. It is therefore to be understood that within the scope of the appended claims, the invention may be practiced otherwise than as specifically described herein.

The invention claimed is:

1. An optical sensor comprising:
   a core;
   a cladding, the cladding and the core collectively comprising an optical waveguide;
   an over-layer over the cladding having a refractive index greater than that of the cladding;
   a periodic structure in at least one of the core and the cladding; and
   a sensing layer over the over-layer made of a sensing material that has an index of refraction that changes as a function of ambient environment.

2. An optical sensor according to claim 1, wherein the over-layer is adapted to serve as a sensitivity enhancement layer.

3. An optical sensor according to claim 1, wherein the optical sensor is formed on a planar substrate.

4. An optical sensor according to claim 3, wherein the cladding comprises a first cladding layer and a second cladding layer, the first cladding layer being in close proximity to the planar substrate and the second cladding layer being in close proximity to the over-layer.

5. An optical sensor according to claim 1, wherein the optical sensor is formed on an optical fiber.

6. An optical sensor according to claim 1, a notch wavelength shift as a function of over-layer thickness has at least one section with relatively poor sensitivity enhancement, at least one section with relatively good sensitivity enhancement, and at least one section that is systemically poor for sensing, and wherein the over-layer thickness is selected to be in the at least one section with relatively good sensitivity enhancement.

7. An optical sensor according to claim 2, wherein a notch wavelength shift as a function of over-layer thickness has at least one section with relatively poor sensitivity enhancement, at least one section with relatively good sensitivity enhancement, and at least one section that is systemically poor for sensing, and wherein the over-layer thickness is selected to be in the at least one section with relatively good sensitivity enhancement.

8. An optical sensor according to claim 1 wherein the periodic structure is in the core.

9. An optical sensor according to claim 1 wherein the periodic structure is in the cladding.

10. An optical sensor according to claim 1 wherein the periodic structure is a long-period grating.

11. An optical sensor according to claim 1 wherein the periodic structure is a fiber Bragg grating.

12. The optical sensor of claim 1 further comprising a jacket.

13. The optical sensor of claim 1, wherein the radius of the fiber core is 4.1 µm and the outer radius of the cladding is 62.5 µm.

14. The optical sensor of claim 1, wherein the periodic structure has a step index profile with a relative index difference of 0.34%.

15. The optical sensor of claim 1 wherein the over-layer is deposited on the cladding, and the sensing layer is deposited on the over-layer.

16. The optical sensor of claim 4 wherein the over-layer has an index of refraction greater than the second cladding layer.

17. The sensor of claim 1, wherein the index of fraction and/or thickness of the over-layer are selected to optimize operating conditions such as sensitivity, refractive index of the sensing layer.

18. Apparatus for determining a measurable parameter experienced by a remote light sensor comprising:

a light source, an optical sensor for receiving light transmitted by the light source, the optical sensor comprising a core, a cladding, the cladding and the core collectively comprising an optical waveguide and an over-layer over the cladding having a refractive index greater than that of the cladding, a sensing layer over the over-layer made of a sensing material that has an index of refraction that changes as a function of ambient environment; the optical sensor further comprising a periodic structure in at least one of the core and the cladding;

a detector for receiving a light signal output by the optical sensor.

19. The apparatus of claim 18, wherein the index of fraction and/or thickness of the over-layer are selected to optimize operating conditions.

20. A method comprising:

immersing an optical sensor in an ambient environment, the sensor comprising a core, a cladding, the cladding and the core collectively comprising an optical waveguide, an over-layer having a refractive index greater than that of the cladding; a periodic structure in at least one of the core and the cladding, and a sensing layer made of a sensing material that has an index of refraction that changes as a function of ambient environment;

inputting a broadband light source to the sensor; and measuring a transmission spectrum characteristic and mapping the transmission spectrum characteristic to a characteristic of the ambient environment.

* * * * *